(12) United States Patent
Arp (10) Patent No.: US 9,063,000 B2
(45) Date of Patent: Jun. 23, 2015

(54) USING THERMAL IMAGING FOR CONTROL OF A MANUFACTURING PROCESS

(75) Inventor: Zane A. Arp, Collegeville, PA (US)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 799 days.

(21) Appl. No.: 13/319,535

(22) PCT Filed: May 13, 2010

(86) PCT No.: PCT/US2010/034658
§ 371 (c)(1),
(2), (4) Date: Nov. 9, 2011

(87) PCT Pub. No.: WO2010/132634
PCT Pub. Date: Nov. 18, 2010

(65) Prior Publication Data
US 2012/0057018 A1    Mar. 8, 2012

Related U.S. Application Data (60) Provisional application No. 61/178,540, filed on May 15, 2009, provisional application No. 61/233,593, filed on Aug. 13, 2009.

(51) Int. Cl.
*H04N 7/18* (2006.01)
*A61J 1/00* (2006.01)
*G01J 5/00* (2006.01)
(Continued)

(52) U.S. Cl.
CPC .............. *G01J 5/0022* (2013.01); *A61J 3/005* (2013.01); *A61J 3/10* (2013.01); *B01J 2/006* (2013.01); *B01J 2/02* (2013.01); *B01J 2/16* (2013.01); *B01J 2/20* (2013.01); *G01J 5/041* (2013.01);
(Continued)

(58) Field of Classification Search
CPC ................ A61J 1/00; A61K 1/00; H04N 7/18
See application file for complete search history.

(56) References Cited

U.S. PATENT DOCUMENTS 4,111,626 A * 9/1978 Funakoshi et al. ............ 425/203
6,690,016 B1 * 2/2004 Watkins et al. ............ 250/341.7
(Continued)

FOREIGN PATENT DOCUMENTS

JP          5-293357 A    11/1993
JP   H19920122599   * 11/1993 ................ A61J 3/10
JP        2002-95950 A    4/2002

OTHER PUBLICATIONS

Bultmann, et al. *The AAPS Journal*, 7 (Supplement 2) (2005). Retrieved from the Internet: http://www.aapsj.org/abstracts/AM_2005/AAPS2005-001464.pdf.

*Primary Examiner* — Christopher S Kelley
*Assistant Examiner* — Deirdre Beasley
(74) *Attorney, Agent, or Firm* — Dara L. Dinner; Theodore Furman (57) ABSTRACT

A thermal imaging camera monitors the temperature different zones in a pharmaceutical process such as ribbon compaction, coating, spray drying, fluid bed drying, high shear wet granulation, crystallization, lyophilization, precipitation, fermentation, and low dosage dispensing of a pharmaceutically active liquid. The thermal imaging camera can be used to produce a visual display of a temperature profile, or a spray pattern. In addition, feedback from the thermal imaging camera is used to control one or more processing parameters.

15 Claims, 9 Drawing Sheets

(51) Int. Cl.
  *B01J 2/00* (2006.01)
  *B01J 2/02* (2006.01)
  *B01J 2/16* (2006.01)
  *B01J 2/20* (2006.01)
  *G01J 5/04* (2006.01)
  *G01J 5/08* (2006.01)
  *A61J 3/00* (2006.01)
  *A61J 3/10* (2006.01)

(52) U.S. Cl.
  CPC ............... *G01J 5/08* (2013.01); *G01J 5/0893* (2013.01); *G01J 2005/0085* (2013.01)

(56) References Cited

U.S. PATENT DOCUMENTS

| | | | |
|---|---|---|---|
| 8,577,120 B1* | 11/2013 | Koshti | 382/141 |
| 2002/0140563 A1* | 10/2002 | Hayward | 340/584 |
| 2003/0004470 A1* | 1/2003 | Hickerson et al. | 604/251 |
| 2003/0042248 A1* | 3/2003 | Witt et al. | 219/497 |
| 2003/0065414 A1* | 4/2003 | van den Nieuwelaar et al. | 700/97 |
| 2003/0183229 A1* | 10/2003 | Smith et al. | 128/203.12 |
| 2004/0214746 A1* | 10/2004 | Bosch et al. | 514/1 |
| 2006/0017916 A1* | 1/2006 | Clarke et al. | 356/300 |
| 2006/0102024 A1* | 5/2006 | Ono et al. | 101/128.4 |
| 2006/0124656 A1* | 6/2006 | Popovich | 221/9 |
| 2007/0098931 A1* | 5/2007 | Bunick | 428/34.1 |
| 2008/0069880 A1* | 3/2008 | Bunick | 424/472 |
| 2008/0093764 A1* | 4/2008 | Ito et al. | 264/101 |
| 2009/0284603 A1* | 11/2009 | Hsieh | 348/164 |
| 2009/0294673 A1* | 12/2009 | Lewis et al. | 250/339.12 |
| 2010/0007877 A1* | 1/2010 | Lewis et al. | 356/326 |
| 2010/0080897 A1* | 4/2010 | Fiesser | 427/212 |
| 2010/0229859 A1* | 9/2010 | Hodson et al. | 128/203.15 |

* cited by examiner

USING THERMAL IMAGING FOR CONTROL OF A MANUFACTURING PROCESS

CROSS-REFERENCE TO RELATED APPLICATION

This application is a §371 national stage entry of International Application No. PCT/US2010/034658, filed 13 May 2010, which claims the benefit of U.S. Provisional Application Nos. 61/178,540, filed 15 May 2009 and 61/233,593, filed 13 Aug. 2009, which are incorporated herein in their entireties.

FIELD OF THE INVENTION

This invention relates generally to the manufacture of chemical products such as pharmaceutical products, and particularly to the use of thermal imaging to monitor, and optionally, control, a variety of material processing operations such as roller compaction, tablet coating, fluid bed drying, spray drying, lyophilization, crystallization, precipitation, fermentation, and preparation of low dosage pharmaceutical products using liquid dispensing technology.

BACKGROUND OF THE INVENTION

In the manufacture of pharmaceutical products, it is common to utilize an apparatus known as a "roller compactor" to compress a powder composition into a ribbon or into pellets for further processing or utilization. In a roller compactor, the powder composition is fed into a nip between the peripheries of two opposed, counterrotating, rollers.

Feeding can be effected by any of a variety of feeding devices. Typical feeding devices include a screw feeder, which can have a single rotating screw, or a plurality of intermeshing screws, belt conveyors, which can have one or more endless belts, and various other forms of conveying devices suitable for transporting a powder.

The peripheries of the rollers can be simple cylindrical surfaces, or they can have mold cavities in which the powder is compacted and formed into a desired shape. In the case of rollers having simple cylindrical surfaces, the product of the roller compactor is typically in the form of a ribbon of compacted powder, which can be broken up, if desired, by a cutting device. On the other hand, if the rollers have mold cavities in their peripheries, they can deliver discrete pellets of compacted powder.

Roller compaction has been successful for producing various pharmaceutical products. However, product quality problems have been encountered. It is possible to overcome these problems by making adjusting various parameters of the operation of the compactor, but doing so is difficult and requires a great deal of operator experience. In addition, some materials that are highly temperature sensitive, and materials that are processed at temperatures near their melting point are particularly susceptible to problems when subjected to roller compaction.

In tablet coating, which is typically carried out by spraying a coating onto a bed of tablets being tumbled in a rotating drum-like device known as a "coating pan" coating conditions such as the spraying rate, and the rate of evaporation of the coating vehicle, affect tablet temperature. Accordingly measurement of tablet temperature is useful in monitoring the coating operation and in controlling various coating parameters. Heretofore, temperature measurement in coating pans has been carried out using various forms of thermometers such as non-contact infrared temperature measurement devices and other forms of temperature probes. It has also recently been proposed to incorporate into a bed of tablets one or more mobile temperature measurement devices, each having the size, shape, and weight of one of the tablets being coated, and containing a temperature measuring device coupled to a miniature telemetry transmitter for sending temperature data to a remote receiver as a modulated radio signal.

The known temperature measurement devices used for monitoring coating processes do not provide sufficient information for good control of the coating operation, or for designing large coaters by "scaling up" on the basis of temperature measurements taken using a smaller experimental coater. In particular, known temperature measurement devices used in coaters provide little information concerning the coater spray pattern, and are therefore of limited use in determining the relationship between the rate of flow of coating material through the spray nozzles and the amount of coating deposited on the tablets.

In fluid bed drying, where warm air is caused to flow upward through a bed of particulate material in a drying vessel, the temperature of the material tends to stratify, so that the temperatures in the lower parts of the dryer are higher than the temperatures in the upper parts. At the start of a drying operation, the temperature differences between different levels are large. However, as drying proceeds, the temperatures in the upper parts of the dryer increase, and the temperature differences between the upper and lower parts tend to decrease. Thus, early in a drying operation, the temperature difference is high. However, when new material is introduced into the fluid bed dryer, whether in a continuous feed mode or in a batch mode, the temperatures in the upper zones of material become higher. The result is either that excessive drying occurs in the upper zones of the dryer, or the time required for drying decreases. The latter is of course the more desirable result.

The temperature differentials in a fluid bed dryer can be observed using conventional thermal probes. However, conventional probes do not provide adequate information concerning the progressive changes in temperature differentials that occur over time to enable an operator to control drying parameters such as air temperature, material flow, and drying time.

In high shear wet granulation, a powder is subjected to the action of a moving blade in the presence of a binder applied to the material by spraying through one or more spray nozzles. The cooling that occurs due to evaporation of the binder affects the granulation process, but does not take place uniformly within the granulator. Cooling is also affected by the spray pattern of the nozzles. Conventional temperature probes cannot adequately monitor the temperature variations in the material, which can occur both at the surface of the bed as a function of the spray pattern as in a coating operation, and within the bed, as in fluid bed drying.

In spray drying, a slurry of material is sprayed through a nozzle into an atmosphere of heated air, which passes through an exhaust outlet. Conventional temperature measurement techniques used in spray drying measure the temperature of the air at the exhaust outlet, and provide only an indirect, and somewhat unreliable, indication of the actual temperature of the sprayed material as it is being dried. These conventional techniques also lack the ability to monitor the spray characteristics and the temperature profiles within the spray pattern.

In lyophilization, quantities of a wet material are typically placed in a relatively large number of small vials, which are arranged on one or more racks in a chamber in which temperature and pressure can be controlled. The material is first frozen. Then, the pressure and temperature in the chamber are adjusted to a level at which the water in the frozen material sublimes. Thereafter, residual moisture is removed by applying a vacuum while maintaining the material at a controlled temperature.

In a lyophilization chamber, the duration of each of the above steps is typically determined by measurement of the temperature in selected vials. However, the materials in the vials tend to dry at different rates depending on their location within the chamber, and also depending on the materials themselves, which are not necessarily identical. Therefore, temperature measurement in selected representative vials does not always lead to optimal results.

In the preparation of low dosage pharmaceutical products using liquid dispensing technology, an array of pharmacologically inert carrier tablets or similar substrates is transported past an array of dispensing nozzles that project very small, but accurately controlled doses of an active pharmaceutical substance onto the carriers individually. The droplets are typically in the form of liquids containing the active substance either in solution or in suspension. The droplets form coatings on the carriers, which adhere to the carriers. The carriers are typically subjected to heating to evaporate the liquid component of the coatings. Liquid dispensing technology or "LDT" is described in United States Patent Publication 2006/0017916, published Jan. 26, 2006, the entire disclosure of which is herein incorporated by reference.

In liquid dispensing technology, as in the other processes mentioned above, the temperatures of different carriers in the array of carriers moving past the dispensing nozzles can vary from one carrier to another, and if the heating of the carriers for evaporation of the liquid component of the coatings is not properly controlled, some carriers and the active material adhering thereto could be overheated or others could be insufficiently heated to evaporate the solvent or suspension medium.

Other manufacturing processes in which temperature measurement is utilized include crystallization, precipitation, fermentation and the like, in all of which both spatial and temporal temperature variations occur, often in unpredictable patterns.

SUMMARY OF THE INVENTION

The manufacturing process in accordance with a first aspect of the invention comprises three steps, which are not necessarily sequential. First a material, such as a pharmaceutical material, is subjected to processing in which the temperatures of plural different regions of the material are caused to differ from one another. These plural regions, which can be, but are not necessarily, all of the regions of the quantity of material, are scanned using a thermal imaging camera. In the scanning step, a set of data is generated, representing the temperatures at multiple locations within each of the scanned regions. Processing can then be controlled in response to the data generated in the scanning step, and, in the controlling step, at least one processing parameter is adjusted in response to variations in the data. The processing stage can be controlled in real time so that a quantity of material being processed is directly affected by adjustment of processing parameters on the basis of data acquired from that same quantity of material. Alternatively, for example in a batch process, temperature data derived by scanning a first batch of material can be used to determine operating parameters for subsequent process a second and different batch of material.

The invention is particularly advantageous when the manufacturing process is ribbon compaction, coating, spray drying, fluid bed drying, high shear wet granulation, crystallization, lyophilization, precipitation, fermentation, or low dosage dispensing of a pharmaceutically active liquid.

The set of data can be displayed in the form of a two-dimensional image, e.g., a color image on a liquid crystal display screen where the positions on the screen correspond to the locations with in the regions being scanned, and the colors represent the temperatures of the material at those locations. In that case, the control of the at least one process parameter can be carried out by a human operator, who can interpret the displayed image and adjust one or more process parameters according to his or her interpretation of the displayed information.

Alternatively, the set of data generated in the scanning step can be delivered as an electrical signal to an automatic controller, which can control the processing step in response to the electrical signal. The electrical signal can be, for example, an amplitude-varying analog signal, or one or more sequences of digital pulses, representing temperature of various locations in the scanned regions as the regions are scanned repeatedly by the thermal imaging camera.

In one embodiment of the invention, the process is roller compaction. In roller compaction, physical properties, and in some cases chemical properties, of a compacted powder delivered by a roller compactor are dependent on certain operating parameters of the apparatus, including the rate at which the raw powder is fed to the nip, the rate of rotation of the rollers, the spacing of the rollers, and the temperature of the rollers. These same parameters also affect the temperature of the compacted material as it exits the nip of the compactor.

For example, if the rate at which the raw powder is fed to the nip is increased, the pressure applied to the powder will increase, and, as a result, the temperature of the compacted product will increase. If the rate of rotation of the rollers decreases, the temperature of the product can increase for the same reason. On the other hand, if one or both rollers are cooled sufficiently, for example by coolant flow, increasing the dwell time in the nip of the compactor by reducing the rate of rotation of the rollers can result in a decrease in product temperature. The spacing of the rollers can also affect the pressure applied to the powder and thereby affect product temperature. And, of course, coolant temperature can affect product temperature by conduction.

According to the invention, the temperature of the product is measured immediately as it exits the nip of the compactor. The measurement of temperature of the product at the nip exit is made possible by the use of thermal imaging. By measuring the temperature of the compacted material as it exits the nip, it is possible to regulate one or more operating parameters of the compactor, and thereby produce a uniform product having the desired properties. Thermal imaging to measure product temperature at the exit of the nip of the compactor can also be used as an analytical tool for process optimization and failure mode analysis, especially since it enables the operator to observe the effects of the adjustment of each of several operating parameters.

The compactor in accordance with the invention comprises a feeder adapted to receive and transport a powder composition and a pair of counterrotating rollers having opposed peripheral surfaces. The rollers are disposed in relation to the feeder to receive the powder composition transported by the feeder between their opposed peripheral surfaces. The rollers apply pressure to the composition, and deliver, at a delivery location adjacent the rollers, a product consisting of a compressed version of the composition. A thermal imaging camera, aimed at the delivery location, detects the temperature of the product, and provides an output signal representing the temperature of the product. A control connected to the thermal imaging camera, and responsive to its output signal, regulates one or more operating parameters of the compactor. The operating parameters can be the rate at which the powder composition is transported by the feeder, the rate of rotation of the counterrotating rollers, the spacing of the rollers, or the temperature of the rollers.

In the case in which the feed rate is controlled, the compactor preferably includes a motor, responsive to the control, and arranged to operate the feeder, and the control regulates the speed of the motor by decreasing the speed of the motor with increasing product temperature and increasing the speed of the motor with decreasing product temperature.

In the case in which the rate of rotation of the rollers is controlled, the compactor preferably includes a motor, responsive to the control, and arranged to rotate the rollers, and the control regulates the speed of the motor. If the rollers are not chilled, the control preferably increases the speed of the motor with increasing product temperature and decreases the speed of the motor with decreasing product temperature. On the other hand, if the rollers are sufficiently chilled, the control may be set so that it decreases the speed of the motor with increasing product temperature and increases the speed of the motor with decreasing product temperature.

In the case in which the roller spacing is controlled, the compactor preferably includes a spacing adjuster, responsive to the control, for determining the spacing of the rollers from each other, and the control regulates the spacing of the rollers by increasing the spacing of with increasing product temperature and decreasing the spacing with decreasing product temperature.

In the case in which roller temperature is controlled, the compactor preferably includes a temperature adjuster, responsive to the control, for determining the temperature of the rollers, and the control regulates the temperature of the rollers by increasing the temperature of the rollers with decreasing product temperature, and decreasing the temperature of the rollers with increasing product temperature. The control can regulate any desired combination of operating parameters.

In coating, an infrared camera can be used to scan the surface of bed of tablets being tumbled in a coating pan and onto which a coating is being sprayed by one or more nozzles. The temperature in the coating pan is typically controlled by controlling the temperature a supply of air directed through the pan or by controlling the temperature of the coating pan itself. However, evaporation of solvent in the coating material causes cooling. Because of evaporative cooling, thermal imaging can be used to monitor the spray pattern to detect nozzle clogging, and also to determine empirically, based on the area of the bed being coated as shown by the thermal image, and on previously accumulated data, the rate at which coating material is being deposited onto the tablets, and control of the spraying rate or other processing parameters can be carried out in response to the data derived from the thermal imaging camera.

The ability of the thermal imaging camera to monitor spray patterns can also be utilized to gain a better understanding of the manner in which coating material is deposited over time, and this information can be used in scaling up, i.e., in the design of larger coating apparatuses.

In fluid bed drying, thermal imaging can be utilized to monitor the temperature profile of a dryer, thereby making it possible to carry out drying more efficiently by reducing drying time as the temperatures in the upper levels within the bed of material being dried progressively increase over time.

In high shear wet granulation, a thermal imaging camera can be used to monitor the temperature at the surface of the material being processed to monitor the pattern of sprayed binder by observing its evaporative cooling as in the coating process discussed above. In addition, a thermal imaging camera can be used to monitor the temperature profile in the granulation bowl and to detect excessive heating resulting from the use of more shearing power than is necessary.

In the case of spray drying, thermal imaging makes it possible to obtain a direct measure of the temperature of the slurry of material as it exits the spray nozzle for improved control of processing parameters such as air supply rate, air supply temperature, and spraying pressure. The thermal imaging camera can be positioned outside the dryer as in the case of a fluid bed dryer to monitor temperature profiles, or inside the dryer, where it can be used to monitor the temperature of the material being sprayed and also to monitor the spray pattern.

In lyophilization, thermal imaging camera can observe the temperatures of numerous lyophilization vials on a rack at the same time, and detect differences in temperature from one vial to another in order to control various parameters such as vacuum, temperature and times for the several stages in the lyophilization cycle so that optimum drying takes place without detriment to the product.

In preparation of pharmaceutical products using liquid dispensing technology, the temperatures of a large number of carriers in an array to which droplets are applied can be monitored, and temperature differences can be detected so that process parameters can be controlled to avoid overheating and insufficient heating.

Various other applications of thermal imaging in material processing, and other details and advantages of the invention will be apparent from the following detailed description when read in conjunction with the drawings.

DETAILED DESCRIPTION OF THE PREFERRED EMBODIMENTS

Figure 1:
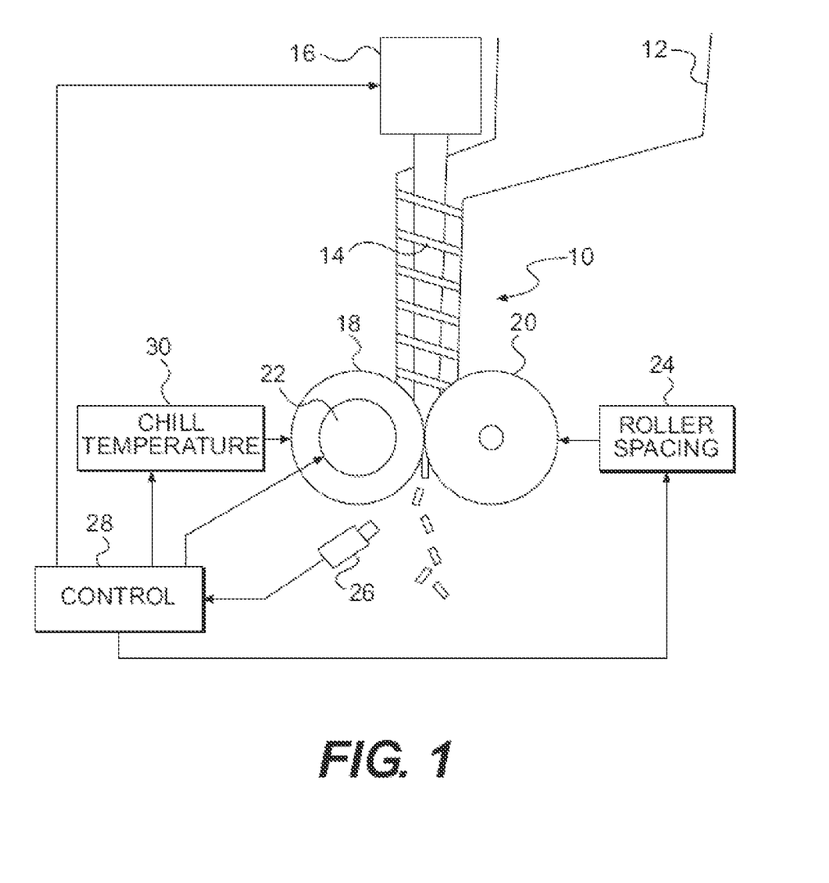
FIG. 1 is a schematic view showing a roller compactor equipped with a thermal imaging camera and a control responsive to the thermal imaging camera for regulating various operating parameters of the roller compactor.

As shown in FIG. 1, a roller compactor 10 is provided with a hopper 12, for receiving material to be compacted. Material is fed from the hopper, by a feed screw 14 rotated by a motor 16, toward a pair of rollers 18 and 20, which have their outer peripheral surfaces in opposed relationship adjacent the lower end of the feed screw 14. The peripheral surfaces of the rollers can be formed with recesses for molding the material fed by the screw 14 into pellets, and can have various other surface configurations, depending on the desired result. The peripheral surfaces of the rollers can also be simple cylinders.

Roller 18 is rotated by a motor 22, and coupled by gears or other suitable drive means (not shown) to roller 20, so that both rollers rotate in opposite directions, but at the same peripheral speed.

An actuator 24, connected to roller 20, is provided to control the relative positions of the axes of rotation of the rollers, and thereby adjust the roller spacing.

In a roller compactor one or both of the rollers is typically provided with internal passages for flow of a cooling liquid. In this case, the cooling liquid temperature is maintained at a desired level by means of a chill temperature control 30.

A thermal imaging camera 26 is aimed at the exit of the nip between rollers 18 and 20, so that it can continuously monitor the temperature of the product immediately as it is delivered by the compactor. By the use of conventional gating techniques on the camera output signal, or by other electronic selection techniques, it is possible to select a portion of the image and to derive a temperature signal from only that portion of the image. By selecting the portion of the image that corresponds to the product, and rejecting the portion of the image that corresponds to the rollers and any other surrounding components, the temperature monitoring apparatus can discriminate between the temperature of the product and the temperature of the rollers and other components, and thereby obtain an accurate and continuous measurement of product temperature. The selection is carried out in control apparatus 28.

The control apparatus 28 also provides speed control signals to the feed screw drive motor 16 and the roller drive motor 22, and provides additional control signals to the roller spacing actuator 24 and the chill temperature control 30. These four control signals will ordinarily be utilized individually. However, they can be used in any combination. When the signals are used in combination, their relative magnitudes should be set so that each signal has the desired effect and so that overshoot is avoided.

When the control apparatus 28 controls the speed of roller drive motor 22, whether or not the motor speed is set to vary directly or inversely with the monitored product temperature will depends on whether or not the rollers are cooled and on the extent to which they are cooled. If the chill temperature control 30 is operative, and a sufficient cooling effect is sufficiently high, it will be desirable to set the control 28 so that the speed of motor 22 varies inversely with product temperature. Thus, if the roller 18 is sufficiently cool, the roller speed can decrease with increasing product temperature. Doing so will increase the product dwell time in the roller nip and maintain a constant product temperature. A similar inverse relationship between roller speed and product temperature can be utilized when the rollers are cooled without feedback to the cooler form the thermal imaging camera.

The thermal imaging camera can also be used to monitor product temperature without controlling any of the operating parameters feedback. In this case, the effects of adjustment of operating parameters such as feed rate, roller speed, roller spacing, and chill temperature can be determined by varying each parameter individually while holding the others at predetermined constant values. By monitoring the effects of operating parameters in this manner, data on the performance of a given compactor can be recorded and utilized in its future operation for process optimization.

The apparatus depicted in FIG. 1 is only one example of various compactors in which the principles of invention can be utilized.

The particular feeder shown in FIG. 1, utilizes a single feed screw, tapered to produce some initial compaction of the powder before it reaches the rollers. The feeder can take various other forms which, for the purposes of this invention, are equivalents of the screw feeder shown. For example, the feeder can utilize a straight, non-tapered, screw, or a screw, either tapered or non-tapered, having a varying pitch, preferably one in which the turns of the screw are progressively closer together as the conveyed material approaches the rollers. Other equivalent feed devices such as belt conveyors incorporating a single conveyor belt, two belts opposed to each other, or other belt arrangements, can be used. Any of numerous other conveyors suitable for transporting powdered material can also be used and are equivalent to the screw conveyor shown in FIG. 1.

The motors 18 and 22 are preferably electric motors such as DC servomotors, or the like. The motors may be equipped with suitable speed reduction gears or other transmissions if necessary. However, hydraulic motors, and other forms of motors, such as turbines, etc. can be used and, so long as their speeds can be controlled, they are considered equivalents of the motors described.

The rollers 18 and 20 can be any suitable compacting rollers having opposed peripheral surfaces. The peripheral surfaces can be cylindrical, or can have suitable recesses or other surface configurations. While the rollers are preferably circular, rollers having various non-circular shapes, can be utilized so long as their peripheral surfaces cooperate to form a suitable compacting nip. Likewise, the rollers can be tapered in the same direction, in which case, their axes will not be parallel, or tapered in opposite directions. The rollers need not be the same size, and more than two rollers can be used in some compactor configurations. Any such arrangement can be considered equivalent to the rollers shown for the purpose of this invention.

The roller spacing actuator 24 can be any suitable actuator, such as an electrically operated linear actuator having a rotary motor-and-rack and pinion gearing. However any of various other forms of actuator, such as a hydraulic actuator or the like can be utilized, and, for the purpose of this invention are equivalent to an electrically operated linear actuator.

The chill temperature control 30 is preferably a refrigeration device having a heat exchange coil through which liquid is circulated to one or both rollers through rotary seals or other suitable coupling devices. In the apparatus shown, the coolant is preferably circulated through the interior of roller 18. However, coolant can be made to flow in contact with the exterior of one or both rollers. Alternatively, air cooling, thermoelectric (Peltier effect) cooling, or other forms of cooling can be utilized. All forms of controllable cooling devices suitable for cooling a compaction roller may be considered equivalent to the chill temperature control 30 for the purpose of this invention.

The thermal imaging camera 26 can be any of various forms of thermal imaging camera that provide an output that is effectively an electronic representation of the variations of temperature within the camera's field of view. Preferably the output of the camera is such that information corresponding to a specific selected area in its field of view can be selected and isolated.

The control 28 can be any of various forms of control devices, including microprocessor-based controls, programmed logic array controls, discrete logic controls, and the like.

Various modifications other than those mentioned above can be made. For example, the thermal imaging camera can be aimed along a direction parallel to the axes of the rollers, in which case discrimination between the image of the product exiting the nip and the image of the rollers and other components can be simplified. In addition, suitable temperature shields can be utilized to improve image discrimination.

Figure 2:
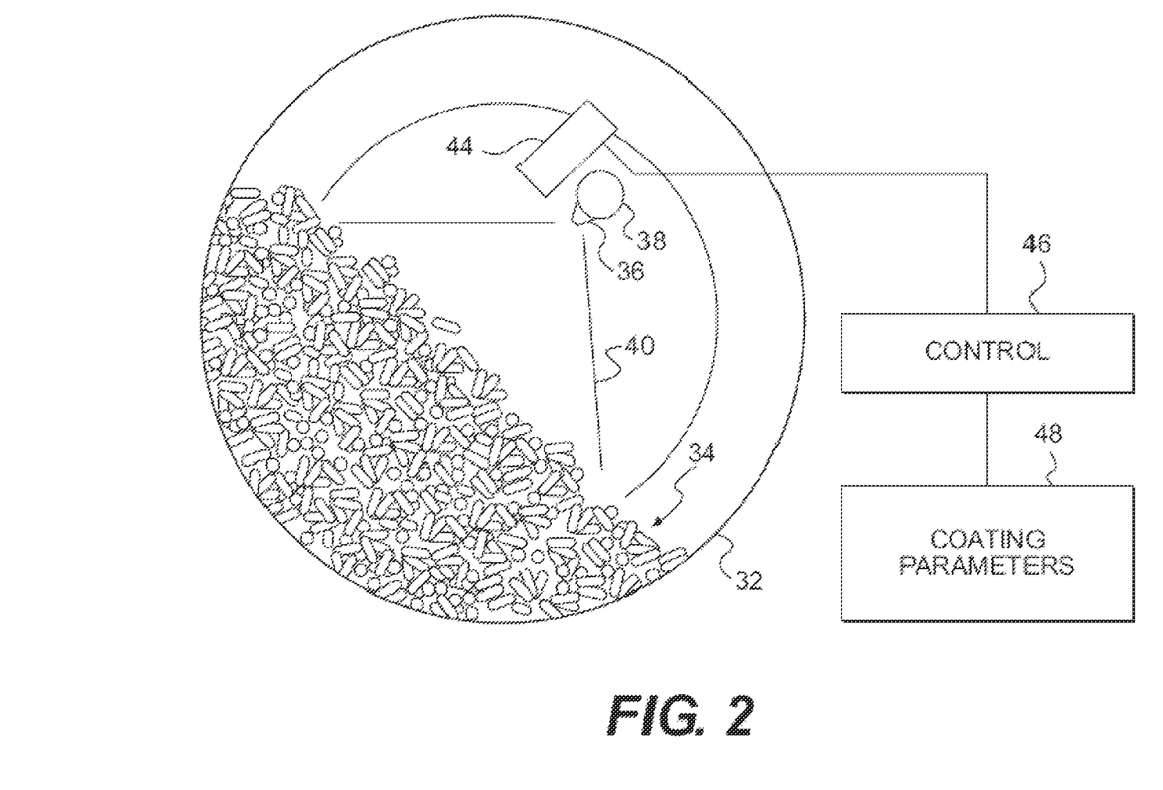
FIG. 2 is a schematic sectional view of a coating apparatus equipped with a thermal imaging camera taken on a plane to which the axis of rotation of the coating apparatus is perpendicular.
Figure 3:
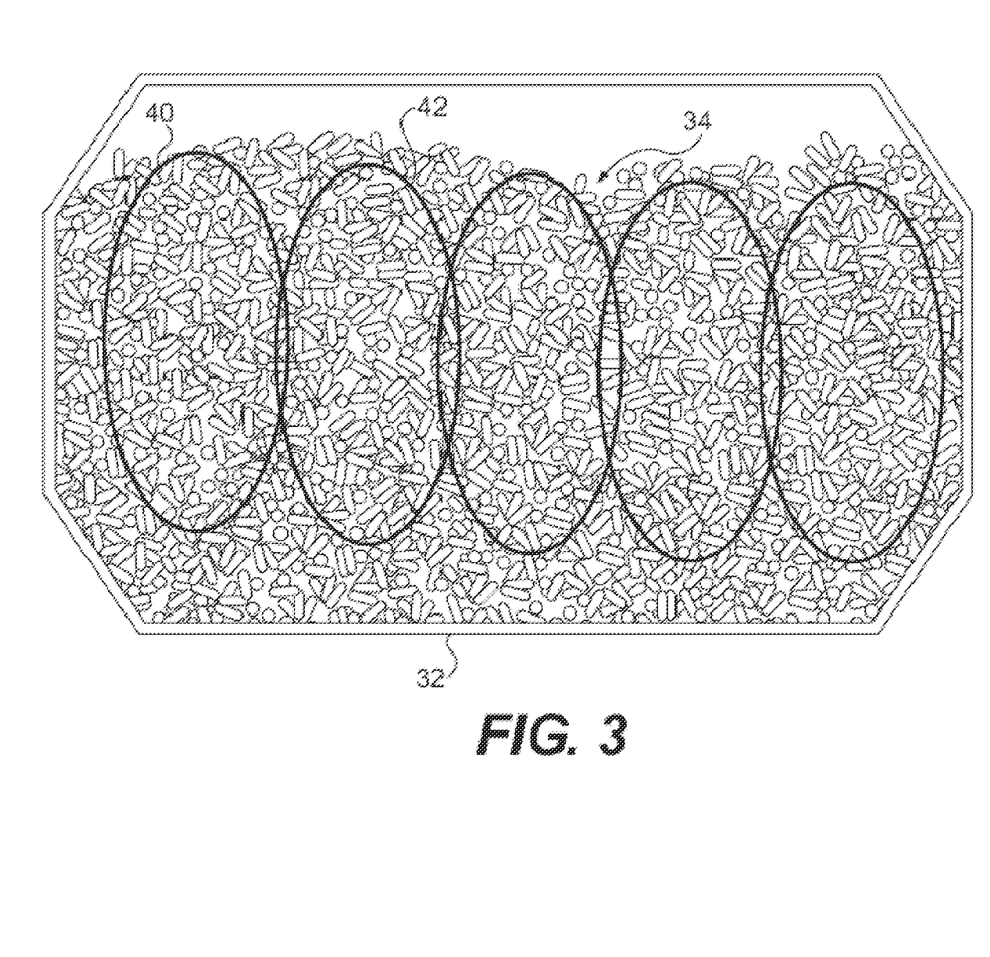
FIG. 3 is a schematic view of the tablet bed in the coating apparatus of FIG. 2, showing a typical spray pattern.

In FIG. 2, as a coating pan 32 rotates clockwise, a bed 34 of tablets within the pan is coated by spraying through a series of nozzles, one of which is shown at 36 on a spray manifold 38. Nozzle 38 delivers a coating solution or suspension to the surface of the tablet bed as the bed is tumbled by rotation of the coating pan. The shape of the spray patter 40 is determined by the nozzle structure, and is typically generally conical. Plural nozzles disposed along the manifold deliver spray patterns 40, 42, etc., which can overlap, as shown in FIG. 3.

A thermal imaging camera 44, located inside the coating pan, and which can be mounted on the spray manifold 38, scans the surface of the tablet bed 34 as the coating is being sprayed. The electrical output of the camera 44 is delivered to a control unit 46, which, in turn, controls one or more coating parameters, which can include the temperature the supply of air directed through the coating pan, the temperature of the coating pan itself, the rate of rotation of the coating pan, spray pressure, spray temperature, and the duration of the coating cycle. Optionally, the output of the thermal imaging camera can be displayed on a screen such as an LCD video screen, so that the temperature of the surface of the tablet bed can be monitored by a human operator.

Because of evaporative cooling of the solvent in the spray (or of the carrier liquid in the case of a suspension), the thermal imaging camera is able to monitor the spray patters accurately. Thus not only is it possible to detect nozzle failure due to clogging, but it is also possible to determine the rate at which coating material is being deposited onto the tablets, and to control of the spray pressure and other processing parameters in response to the data derived from the thermal imaging camera.

As mentioned previously, the ability of the thermal imaging camera to monitor spray patterns can also be utilized to obtain a better understanding the coating process for the purpose of designing larger coating pans on the basis of information obtained from laboratory equipment.

Figure 4:
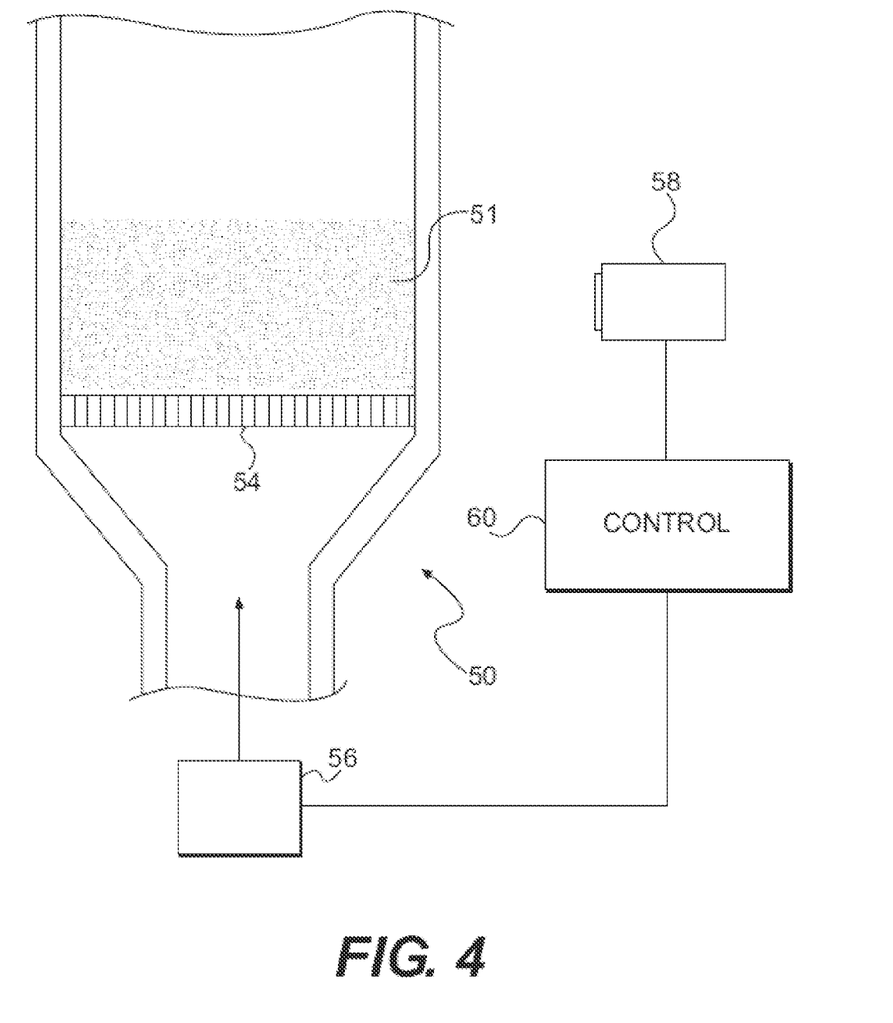
FIG. 4 is a schematic side elevational view of a fluid bed dryer equipped with a thermal imaging camera arranged to obtain a temperature profile.

FIG. 4 shows a fluid bed dryer 50, in which a bed 52 of particles is dried by heated air delivered upward through a perforated support 54 from an air supply 56. The output of a thermal imaging camera 58 disposed on a side of the dryer delivers an output to a control unit 60, which, in turn, can controls operating parameters of the air supply 57 such as air flow rate and temperature. Alternatively, the thermal imaging camera can be used to control drying time, thereby achieving more efficient operation by taking into account changes in the temperature profile of the dryer that take place as successive batches of material are processed and adjusting drying times accordingly. The use of thermal imaging to control processing parameters and/or drying times is applicable to continuous fluid bed dryers as well as to batch mode dryers.

Figure 5:
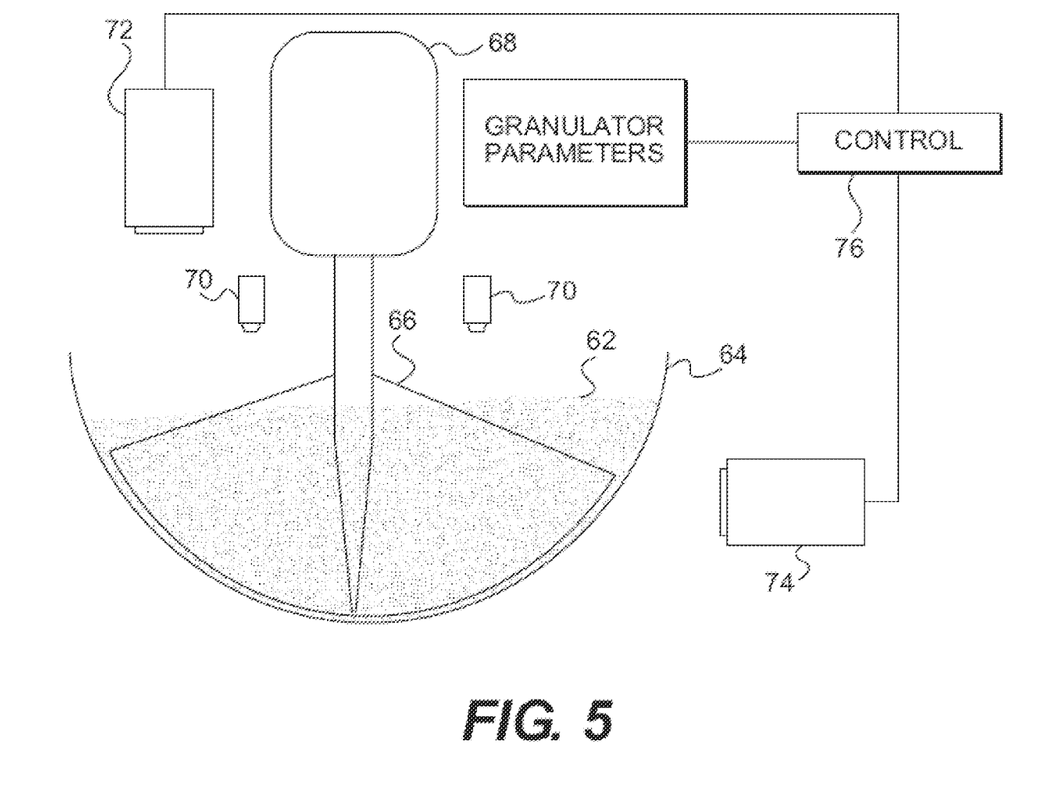
FIG. 5 is a schematic elevational view of a high shear granulator equipped with two thermal imaging cameras, one arranged to scan the surface of the material bed in the granulation bowls, and the other arranged to obtain a temperature profile.

In the high shear wet granulation apparatus as shown in FIG. 5, a bed 62 of material in a bowl 64 is mixed by a set of blades 66 operated by a motor 66, while being sprayed with a liquid binder through one or more spray nozzles 70. A first thermal imaging camera 72 is arranged above the bowl 64 so that it can monitor the temperature at the surface of the material bed 62 and thereby monitor the pattern of sprayed binder by observing its evaporative cooling as in the coating process depicted in FIGS. 2 and 3. A second thermal imaging camera 74 is used to monitor the temperature profile in the granulation bowl 64 and can be used to detect excessive heating resulting from the use of excessive shearing power. Both thermal imaging cameras are connected to a control unit 76, which, in turn, can control various granulator operating parameters, such as binder spray rate, motor speed and processing time.

Figure 6:
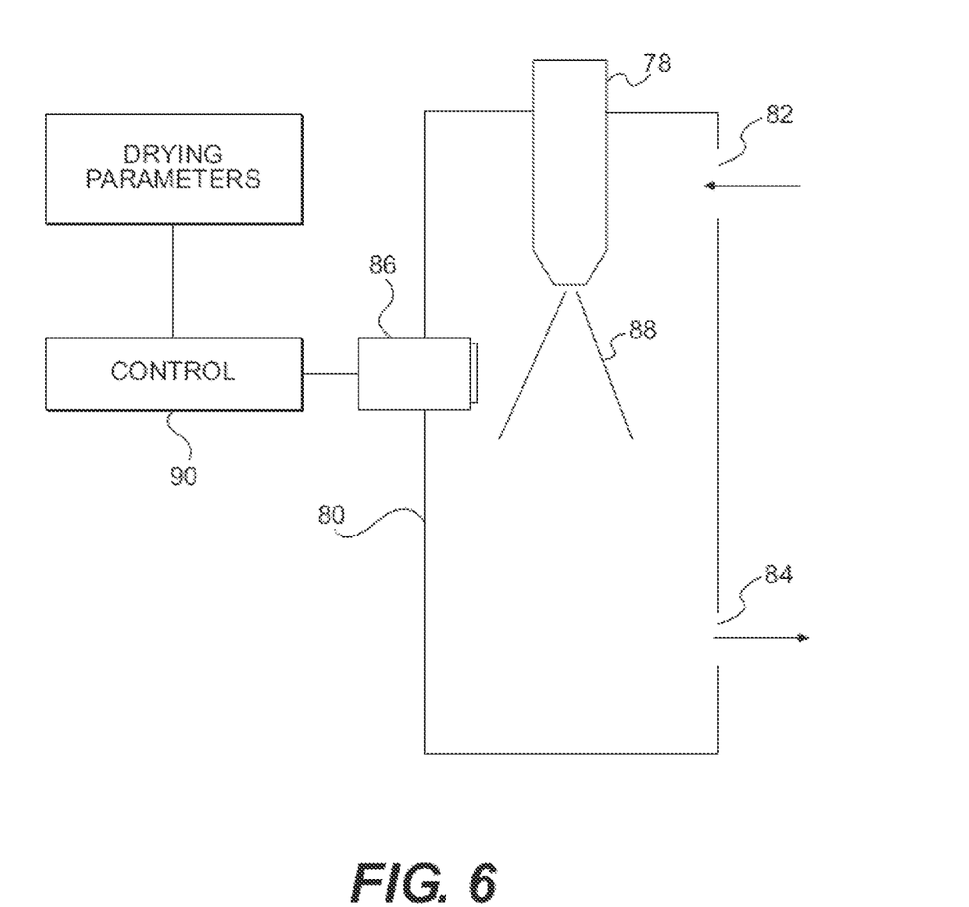
FIG. 6 is a schematic elevational view of a spray dryer equipped with a thermal imaging camera arranged to scan the material being dried as it exits from the spray nozzle of the dryer.

In the spray drying system shown in FIG. 6, a spray nozzle 78 directs a slurry of material to be dried into an enclosure 80 having an air inlet 82 and an air outlet 84. A thermal imaging camera 86 is arranged to scan the spray pattern 88 adjacent the exit of the nozzle and thereby obtain a direct measure of the temperature of the slurry of material as it exits the spray nozzle. The output of the thermal imaging camera is connected to a control unit 90, which can control various processing parameters such as air supply rate, air supply temperature, and spray pressure. As an alternative, the thermal imaging camera can be positioned outside the dryer as in the case of a fluid bed dryer to monitor temperature profiles.

Figure 7:
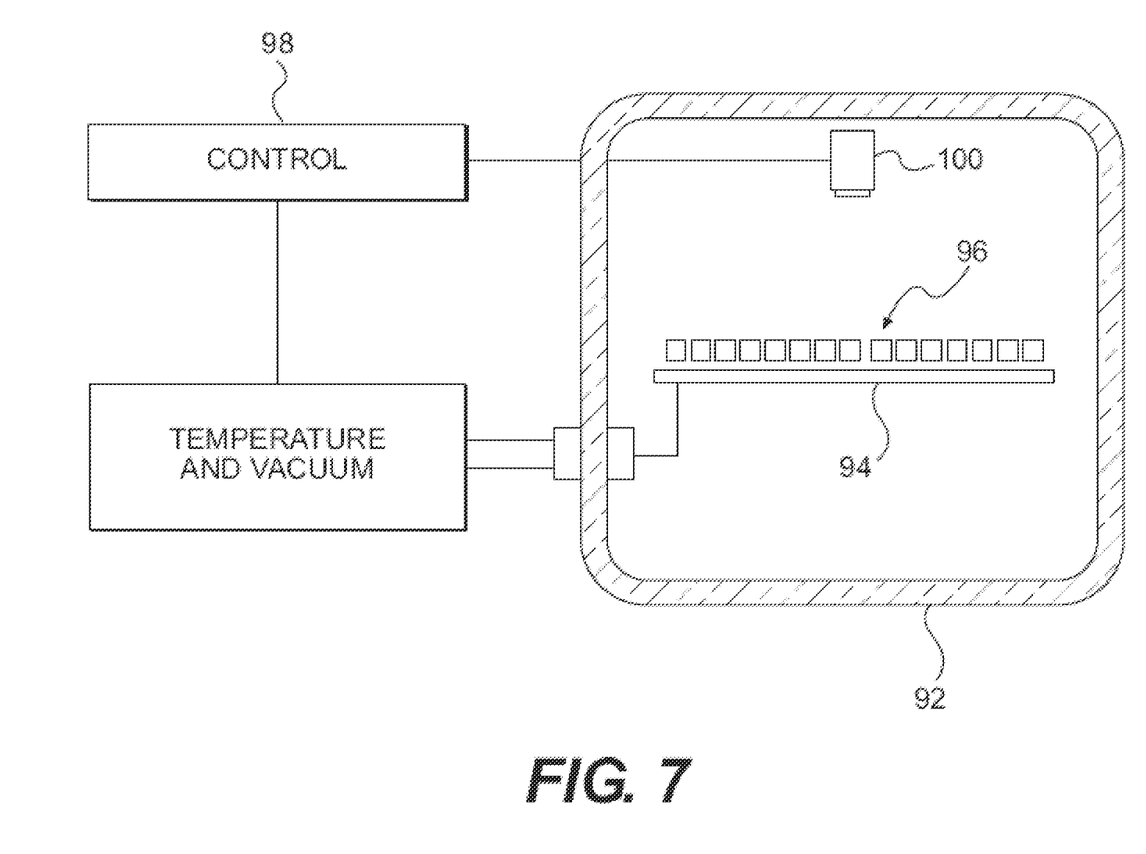
FIG. 7 is a schematic elevational view of a lyophilization chamber equipped with a thermal imaging camera arranged to scan an array of lyophilization vials on a rack within the chamber.

In FIG. 7, an insulated lyophilization chamber contains a rack 94 supporting a three-dimensional array of lyophilization vials 96. The temperature of the rack 94 and the level of vacuum in the chamber 92 are controlled by a control unit 98 in response to a signal derived from a thermal imaging camera 100 inside the chamber and arranged to scan the temperatures of the set of vials in the array. The thermal imaging camera can detect differences in temperature from one vial to another, and can be used to control various parameters such as vacuum, temperature and times for the several stages in the lyophilization cycle so that optimum drying takes place without detriment to the product.

Figure 8:
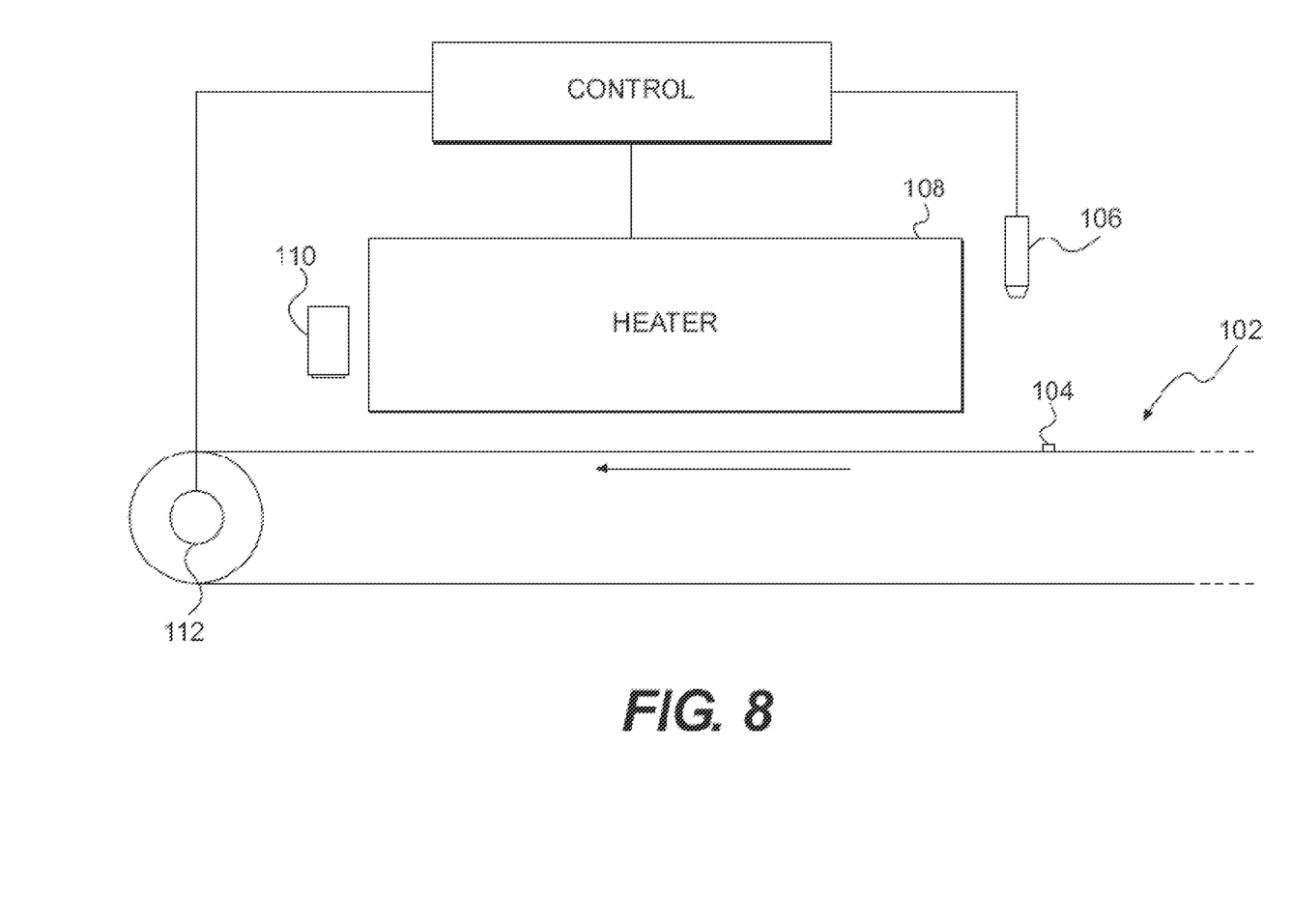
FIG. 8 is a schematic elevational view showing a portion of a low liquid dispensing apparatus equipped with a thermal imaging camera.

FIG. 8 shows a part of a liquid dispensing apparatus for producing low dosage tablets by directing droplets of a pharmaceutically active material onto inert carrier tablets in accurately controlled volumes. The apparatus includes a conveyor which transports rows of carrier tablets, one of which is shown endwise at 104, past a row 106 of dispensing nozzles also shown endwise. The number of nozzles corresponds to the number of carrier tablets in each row. As a row of carrier tablets passes the row of dispensing nozzles, each nozzle directs a droplet of active material onto the carrier. The rows of carrier tablets are then transported underneath a heating apparatus 108. A thermal imaging camera 110 is arranged to scan all the tablets in a row and can detect temperature differences on the basis of which various processing parameters such as heating temperature, and the speed of the conveyor motor 112 can be controlled. In the embodiment shown, the camera is located a short distance downstream from the heating apparatus. Alternatively, the camera can be located inside the heating apparatus.

Figure 9:
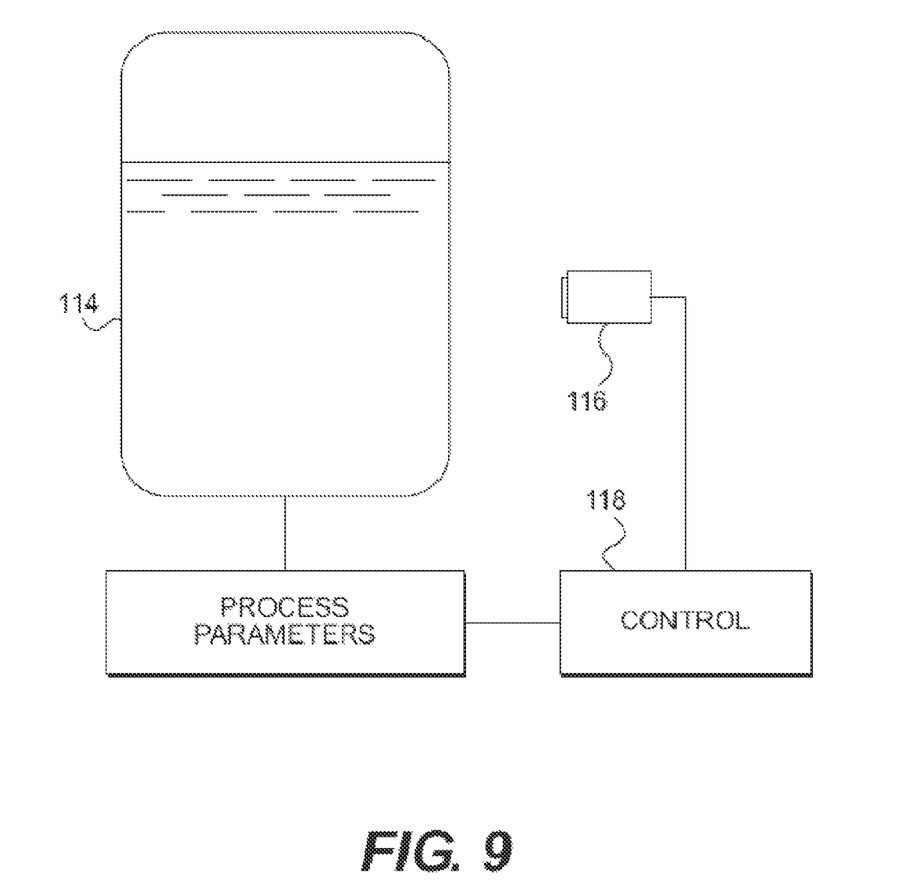
FIG. 9 is a schematic elevational view of a vessel for crystallization precipitation, fermentation or a similar process, equipped with a thermal imaging camera.

In FIG. 9, reference number 114 designates a processing vessel which can be one of a variety of vessels such as a crystallization vessel, a fermentation vessel, a precipitation vessel or the like. The temperature profile of the vessel is monitored by a thermal imaging camera 116 located to the side of the vessel. The thermal imaging camera delivers its output to a control unit 118, which is used to control one or more processing parameters such as temperature and processing time.

In each of the embodiments described above, the thermal imaging camera can be used to provide data from which processing parameters can be controlled using conventional control techniques, both analog and digital. Thermal imaging can be used to produce a visual display of a temperature profile, spray pattern or the like for human observation, and for human intervention in the control loop. Various modifications can be made to the apparatus and processes described. It is possible to utilize multiple thermal imaging cameras to observe separately different regions of a material undergoing processing, as in the case of a lyophilization chamber having multiple racks at different levels, for example. Feedback from the thermal imaging camera can be utilized for real time control of processing parameters, and thermal imaging data derived form a processing operation on a quantity of material can also be used for determination of parameters for subsequent processing operations on other quantities of the same material.

Still other modifications may be made to the apparatus and methods described above without departing from the scope of the invention as defined in the following claims.

What is claimed is:

1. A compactor for pharmaceutical compositions comprising:
    a feeder adapted to receive and transport a powder composition;
    a pair of counterrotating rollers having opposed peripheral surfaces, the rollers being disposed in relation to the feeder for receiving powder composition transported by the feeder between their opposed peripheral surfaces, applying pressure to said composition, and delivering, at a delivery location adjacent said rollers, a product consisting of a compressed version of said composition;
    a thermal imaging camera, aimed at said delivery location, for detecting the temperature of said product, and providing an output signal representing the temperature of said product;
    a control connected to said thermal imaging camera, and responsive to said output signal, for regulating the spacing of said counterrotating rollers; and
    a spacing adjuster, responsive to said control, for determining the spacing of said rollers from each other, and in which said control regulates the spacing of said rollers by increasing the spacing of said rollers with increasing product temperature and decreasing the spacing of said rollers with decreasing product temperature.

2. A compactor for pharmaceutical compositions comprising:
    a feeder adapted to receive and transport a powder composition; a pair of counterrotating rollers having opposed peripheral surfaces, the rollers being disposed in relation to the feeder for receiving powder composition transported by the feeder between their opposed peripheral surfaces, applying pressure to said composition, and delivering, at a delivery location adjacent said rollers, a product consisting of a compressed version of said composition;
    a thermal imaging camera, aimed at said delivery location, for detecting the temperature of said product, and providing an output signal representing the temperature of said product;
    a control connected to said thermal imaging camera, and responsive to said output signal, for regulating the temperature of said counterrotating rollers; and
    a temperature adjuster, responsive to said control, for determining the temperature of said rollers, and in which the control regulates the temperature of said rollers by increasing the temperature of said rollers with decreasing product temperature, and decreasing the temperature of said rollers with increasing product temperature.

3. A compactor according to claim 1, including a motor, responsive to said control, and arranged to operate said feeder, and in which said control regulates the speed of the motor by decreasing the speed of the motor with increasing product temperature and increasing the speed of the motor with decreasing product temperature.

4. A compactor according to claim 2, including a motor, responsive to said control, and arranged to operate said feeder, and in which said control regulates the speed of the motor by decreasing the speed of the motor with increasing product temperature and increasing the speed of the motor with decreasing product temperature.

5. A compactor according to claim 1, including a motor responsive to said control, and arranged to rotate said rollers, and in which said control regulates the speed of the motor by increasing the speed of the motor with increasing product temperature and decreasing the speed of the motor with decreasing product temperature.

6. A compactor according to claim 2, including a motor responsive to said control, and arranged to rotate said rollers, and in which said control regulates the speed of the motor by increasing the speed of the motor with increasing product temperature and decreasing the speed of the motor with decreasing product temperature.

7. A compactor according to claim 2, including a motor responsive to said control, and arranged to rotate said rollers, and in which said control regulates the speed of the motor by decreasing the speed of the motor with increasing product temperature and increasing the speed of the motor with decreasing product temperature.

8. A compactor according to claim 2, including a spacing adjuster, responsive to said control, for determining the spacing of said rollers from each other, and in which said control regulates the spacing of said rollers by increasing the spacing of said rollers with increasing product temperature and decreasing the spacing of said rollers with decreasing product temperature.

9. A compactor according to claim 1, including a first motor, responsive to said control, and arranged to operate said feeder, and in which said control regulates the speed of the first motor by decreasing the speed of the first motor with increasing product temperature and increasing the speed of the first motor with decreasing product temperature, and a second motor responsive to said control, and arranged to rotate said rollers, in which said control regulates the speed of the second motor by increasing the speed of the second motor with increasing product temperature and decreasing the speed of the second motor with decreasing product temperature.

10. A compactor according to claim 2, including a first motor, responsive to said control, and arranged to operate said feeder, and in which said control regulates the speed of the first motor by decreasing the speed of the first motor with increasing product temperature and increasing the speed of the first motor with decreasing product temperature, and a second motor responsive to said control, and arranged to rotate said rollers, in which said control regulates the speed of the second motor by increasing the speed of the second motor with increasing product temperature and decreasing the speed of the second motor with decreasing product temperature.

11. A compactor according to claim 2, including a motor responsive to said control, and arranged to rotate said rollers, and in which said control regulates the speed of the motor by increasing the speed of the motor with increasing product temperature and decreasing the speed of the motor with decreasing product temperature, a spacing adjuster, responsive to said control, for determining the spacing of said rollers from each other, and in which said control regulates the spacing of said rollers by increasing the spacing of said rollers with increasing product temperature and decreasing the spacing of said rollers with decreasing product temperature.

12. A compactor according to claim 2, including a motor responsive to said control, and arranged to rotate said rollers, and in which said control regulates the speed of the motor by decreasing the speed of the motor with increasing product temperature and increasing the speed of the motor with decreasing product temperature, and a spacing adjuster, responsive to said control, for determining the spacing of said rollers from each other, and in which said control regulates the spacing of said rollers by increasing the spacing of said rollers with increasing product temperature and decreasing the spacing of said rollers with decreasing product temperature.

13. A compactor according to claim 2, including a first motor, responsive to said control, and arranged to operate said feeder, and in which said control regulates the speed of the first motor by decreasing the speed of the first motor with increasing product temperature and increasing the speed of the first motor with decreasing product temperature, a second motor responsive to said control, and arranged to rotate said rollers, in which said control regulates the speed of the second motor by increasing the speed of the second motor with increasing product temperature and decreasing the speed of the second motor with decreasing product temperature, and a spacing adjuster, responsive to said control, for determining the spacing of said rollers from each other, and in which said control regulates the spacing of said rollers by increasing the spacing of said rollers with increasing product temperature and decreasing the spacing of said rollers with decreasing product temperature.

14. A compactor according to claim 2, including a first motor, responsive to said control, and arranged to operate said feeder, and in which said control regulates the speed of the first motor by decreasing the speed of the first motor with increasing product temperature and increasing the speed of the first motor with decreasing product temperature, a second motor responsive to said control, and arranged to rotate said rollers, in which said control regulates the speed of the second motor by decreasing the speed of the second motor with increasing product temperature and increasing the speed of the second motor with decreasing product temperature, and a spacing adjuster, responsive to said control, for determining the spacing of said rollers from each other, and in which said control regulates the spacing of said rollers by increasing the spacing of said rollers with increasing product temperature and decreasing the spacing of said rollers with decreasing product temperature.

15. A compactor for pharmaceutical compositions comprising:
a feeder adapted to receive and transport a powder composition; a pair of counterrotating rollers having opposed peripheral surfaces, the rollers being disposed in relation to the feeder for receiving powder composition transported by the feeder between their opposed peripheral surfaces, applying pressure to said composition, and delivering, at a delivery location adjacent said rollers, a product consisting of a compressed version of said composition;
a thermal imaging camera, aimed at said delivery location, for detecting the temperature of said product, and providing an output signal representing the temperature of said product;
a control connected to said thermal imaging camera, and responsive to said output signal, for regulating the spacing of said counterrotating rollers; and
means for cooling at least one of said rollers, and a motor responsive to said control and arranged to rotate said rollers, and in which said control regulates the speed of the motor by decreasing the speed of the motor with increasing product temperature and increasing the speed of the motor with decreasing product temperature.

* * * * *